(12) United States Patent
Matichuk et al.

(10) Patent No.: US 12,678,076 B2
(45) Date of Patent: Jul. 14, 2026

(54) HEALTH SENSOR USING MULTIPLE LIGHT EMITTING DIODES

(71) Applicant: MedWatch Technologies, Inc., Las Vegas, NV (US)

(72) Inventors: Bruce Matichuk, Alberta (CA); Mike E. Moore, Las Vegas, NV (US)

(73) Assignee: MedWatch Technologies, Inc., Las Vegas, NV (US)

( * ) Notice: Subject to any disclaimer, the term of this patent is extended or adjusted under 35 U.S.C. 154(b) by 573 days.

(21) Appl. No.: 18/195,308

(22) Filed: May 9, 2023

(65) Prior Publication Data

US 2023/0355145 A1    Nov. 9, 2023

Related U.S. Application Data

(60) Provisional application No. 63/339,721, filed on May 9, 2022.

(51) Int. Cl.
A61B 5/1455      (2006.01)
A61B 5/00        (2006.01)
(Continued)

(52) U.S. Cl.
CPC ...... A61B 5/14552 (2013.01); A61B 5/02055 (2013.01); A61B 5/7267 (2013.01);
(Continued)

(58) Field of Classification Search
CPC ............ A61B 5/14552; A61B 5/02055; A61B 5/7267; A61B 5/282; A61B 5/4266; A61B 5/681; A61B 2562/0238; A61B 2562/066
See application file for complete search history.

(56) References Cited

U.S. PATENT DOCUMENTS 5,715,819 A * 2/1998 Svenson .............. A61B 5/0507
                                                      324/637
9,420,956 B2   8/2016 Gopalakrishnan et al.
(Continued)

FOREIGN PATENT DOCUMENTS

AU      2023229292 A1    10/2024
AU      2023269185 A1    11/2024
(Continued)

OTHER PUBLICATIONS

International Search Report and Written Opinion, (ISRWO), Application No. PCT/US2024/016553, pp. 1-17, dated Jul. 12, 2024.
(Continued)

*Primary Examiner* — Justin Xu
*Assistant Examiner* — Jonathan M Haney
(74) *Attorney, Agent, or Firm* — James Scott Nolan

(57) ABSTRACT

Near Infrared Spectroscopy (NIS) is employed to non-invasively detect health-related conditions, such as blood glucose concentrations, and accounting for non-linear interference from human tissues, the differences among individuals, and multiple interfering compounds within blood. A multi-layered artificial neural network can be used to assess these relationships and accurately estimate blood glucose levels. Diffuse reflectance spectrum at six different wavelengths are analyzed with a neural network, resulting in a correlation coefficient as high as 0.9216 when compared to a standard electrochemical glucose analysis test.

20 Claims, 5 Drawing Sheets

Sensor Assembly

9

8

1: LED 1050nm
2: LED 1200nm
3: LED 1300nm
4: LED 1450nm
5: LED 1550nm
6: LED 1650nm
7: Photodiode 1050nm-1700nm
8: Mounting PCB

(51) Int. Cl.
　　*A61B 5/0205* 　　(2006.01)
　　*A61B 5/282* 　　(2021.01)
(52) U.S. Cl.
　　CPC ............. *A61B 5/282* (2021.01); *A61B 5/4266*
　　　　　(2013.01); *A61B 5/681* (2013.01); *A61B*
　　　　　*2562/0238* (2013.01); *A61B 2562/066*
　　　　　　　　　　　　　　　　　　(2013.01)

(56)　　　　　　References Cited

U.S. PATENT DOCUMENTS

| | | | |
|---|---|---|---|
| 9,554,738 B1 | 1/2017 | Gulati et al. | |
| 9,582,072 B2 | 2/2017 | Connor | |
| 9,750,977 B2 | 9/2017 | Yuen et al. | |
| 9,826,940 B1 | 11/2017 | Lengerich | |
| 10,153,537 B2 | 12/2018 | Baringer et al. | |
| 10,321,873 B2 | 6/2019 | Connor | |
| 10,327,674 B2 | 6/2019 | Hong et al. | |
| 10,512,407 B2 | 12/2019 | Richards et al. | |
| 10,700,774 B2 | 6/2020 | Panther et al. | |
| 10,878,959 B1 | 12/2020 | Reykhert | |
| 10,880,724 B2 | 12/2020 | Song et al. | |
| 10,998,101 B1 | 5/2021 | Tran et al. | |
| 11,029,199 B2 | 6/2021 | Turgeon et al. | |
| 11,096,601 B2 | 8/2021 | Hong et al. | |
| 11,116,448 B1 | 9/2021 | Trapero Martin et al. | |
| 11,141,129 B1 | 10/2021 | Trapero Martin et al. | |
| 11,166,635 B2 | 11/2021 | Trapero Martin et al. | |
| 11,207,025 B1 | 12/2021 | Trapero Martin et al. | |
| 11,357,426 B2 | 6/2022 | Tran | |
| 11,694,533 B2 | 7/2023 | Shelton, IV et al. | |
| 11,754,542 B2 | 9/2023 | Connor | |
| 11,766,216 B2 | 9/2023 | Zilkie et al. | |
| 11,786,251 B2 | 10/2023 | Shelton, IV et al. | |
| 11,806,109 B2 | 11/2023 | Yuen et al. | |
| 2004/0162471 A1* | 8/2004 | Ikeda | A61B 5/14535 600/476 |
| 2006/0127964 A1* | 6/2006 | Ford | A61B 5/4283 435/14 |
| 2006/0211924 A1* | 9/2006 | Dalke | G16H 40/67 600/326 |
| 2009/0105573 A1* | 4/2009 | Malecha | G16H 50/50 600/365 |
| 2013/0053654 A1* | 2/2013 | Caduff | A61B 5/441 600/323 |
| 2015/0119725 A1 | 4/2015 | Martin et al. | |
| 2015/0320588 A1 | 11/2015 | Connor | |
| 2015/0366469 A1* | 12/2015 | Harris | A61B 5/0022 600/301 |
| 2016/0073886 A1 | 3/2016 | Connor | |
| 2016/0081552 A1 | 3/2016 | Wojtczuk et al. | |
| 2016/0084869 A1 | 3/2016 | Yuen et al. | |
| 2016/0113526 A1 | 4/2016 | Nageshwar et al. | |
| 2016/0232811 A9 | 8/2016 | Connor et al. | |
| 2016/0287110 A1 | 10/2016 | Morris et al. | |
| 2016/0325143 A1 | 11/2016 | Yuen et al. | |
| 2016/0378069 A1 | 12/2016 | Rothkopf | |
| 2017/0119287 A1 | 5/2017 | Flitsch et al. | |
| 2017/0156676 A1 | 6/2017 | Ferber et al. | |
| 2017/0164878 A1 | 6/2017 | Connor | |
| 2017/0188864 A1 | 7/2017 | Drury | |
| 2017/0215793 A1 | 8/2017 | Newberry | |
| 2017/0347899 A1* | 12/2017 | Bhushan | A61B 5/6833 |
| 2018/0146870 A1 | 5/2018 | Shemesh et al. | |
| 2018/0242860 A1 | 8/2018 | LeBoeuf et al. | |
| 2018/0288586 A1 | 10/2018 | Tran | |
| 2018/0353137 A1 | 12/2018 | Balajadia et al. | |
| 2019/0030230 A1 | 1/2019 | Connor | |
| 2019/0110751 A1 | 4/2019 | Lee et al. | |
| 2019/0246963 A1 | 8/2019 | Chung et al. | |
| 2019/0247650 A1 | 8/2019 | Tran | |
| 2019/0283247 A1 | 9/2019 | Chang et al. | |
| 2019/0385708 A1 | 12/2019 | Hong et al. | |
| 2020/0075812 A1 | 3/2020 | Konstantatos et al. | |
| 2020/0376198 A1 | 12/2020 | Newberry et al. | |
| 2021/0145334 A1 | 5/2021 | Ferber et al. | |
| 2021/0169345 A1 | 6/2021 | Wasson et al. | |
| 2021/0169417 A1 | 6/2021 | Burton | |
| 2021/0212606 A1 | 7/2021 | Tran | |
| 2021/0282667 A1* | 9/2021 | Pasupuleti | A61B 5/1124 |
| 2021/0293616 A1 | 9/2021 | Capella et al. | |
| 2021/0321942 A1 | 10/2021 | Pushpala et al. | |
| 2021/0330207 A1 | 10/2021 | Richards et al. | |
| 2021/0379388 A1 | 12/2021 | Connor | |
| 2022/0028553 A1 | 1/2022 | Matichuk et al. | |
| 2022/0233102 A1 | 7/2022 | Shelton, IV et al. | |
| 2022/0233119 A1 | 7/2022 | Shelton, IV et al. | |
| 2022/0233135 A1 | 7/2022 | Shelton, IV et al. | |
| 2022/0233136 A1 | 7/2022 | Shelton, IV et al. | |
| 2022/0233151 A1 | 7/2022 | Shelton, IV et al. | |
| 2022/0233191 A1 | 7/2022 | Shelton, IV et al. | |
| 2022/0233214 A1 | 7/2022 | Shelton, IV et al. | |
| 2022/0233241 A1 | 7/2022 | Shelton, IV et al. | |
| 2022/0233252 A1 | 7/2022 | Shelton, IV et al. | |
| 2022/0233253 A1 | 7/2022 | Shelton, VI et al. | |
| 2022/0233254 A1 | 7/2022 | Shelton, IV et al. | |
| 2022/0233267 A1 | 7/2022 | Shelton, IV et al. | |
| 2022/0238197 A1 | 7/2022 | Shelton, IV et al. | |
| 2022/0238216 A1 | 7/2022 | Shelton, IV et al. | |
| 2022/0238235 A1 | 7/2022 | Shelton, IV et al. | |
| 2022/0240869 A1 | 8/2022 | Shelton, IV et al. | |
| 2022/0241028 A1 | 8/2022 | Shelton, IV et al. | |
| 2022/0241474 A1 | 8/2022 | Shelton, IV et al. | |
| 2022/0415476 A1 | 12/2022 | Connor | |
| 2023/0103445 A1 | 4/2023 | Lee et al. | |
| 2023/0284905 A1 | 9/2023 | Matichuk et al. | |
| 2023/0355145 A1 | 11/2023 | Matichuk et al. | |
| 2023/0400327 A1 | 12/2023 | Streem et al. | |
| 2025/0049324 A1 | 2/2025 | Matichuk et al. | |
| 2025/0082234 A1 | 3/2025 | Matichuk et al. | |

FOREIGN PATENT DOCUMENTS

| | | | |
|---|---|---|---|
| CN | 108451513 A | 8/2018 | |
| CN | 110167430 A | 8/2019 | |
| EP | 3387989 A1 | 10/2018 | |
| EP | 4486206 A2 | 1/2025 | |
| IN | 201941006594 A | 11/2020 | |
| KR | 102062646 B1 | 1/2020 | |
| KR | 20220112327 A | 8/2022 | |
| WO | 2020160058 A1 | 8/2020 | |
| WO | 2022231132 A1 | 11/2022 | |
| WO | 2023014653 A1 | 2/2023 | |
| WO | 2023187686 A1 | 10/2023 | |
| WO | 2023220082 A1 | 11/2023 | |
| WO | 2024173947 A1 | 8/2024 | |

OTHER PUBLICATIONS

International Searching Authority of the PCT; "Notification of Transmittal of the International Search Report and Written Opinion of the International Searching Authority, or the Declaration" dated Aug. 4, 2023; PCT Application No. PCT/US23/21579 filed May 9, 2023; pp. 1-7 (2023).

* cited by examiner

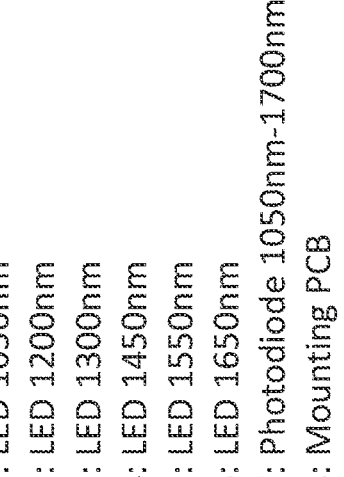
1: LED 1050nm
2: LED 1200nm
3: LED 1300nm
4: LED 1450nm
5: LED 1550nm
6: LED 1650nm
7: Photodiode 1050nm-1700nm
8: Mounting PCB
FIG. 1
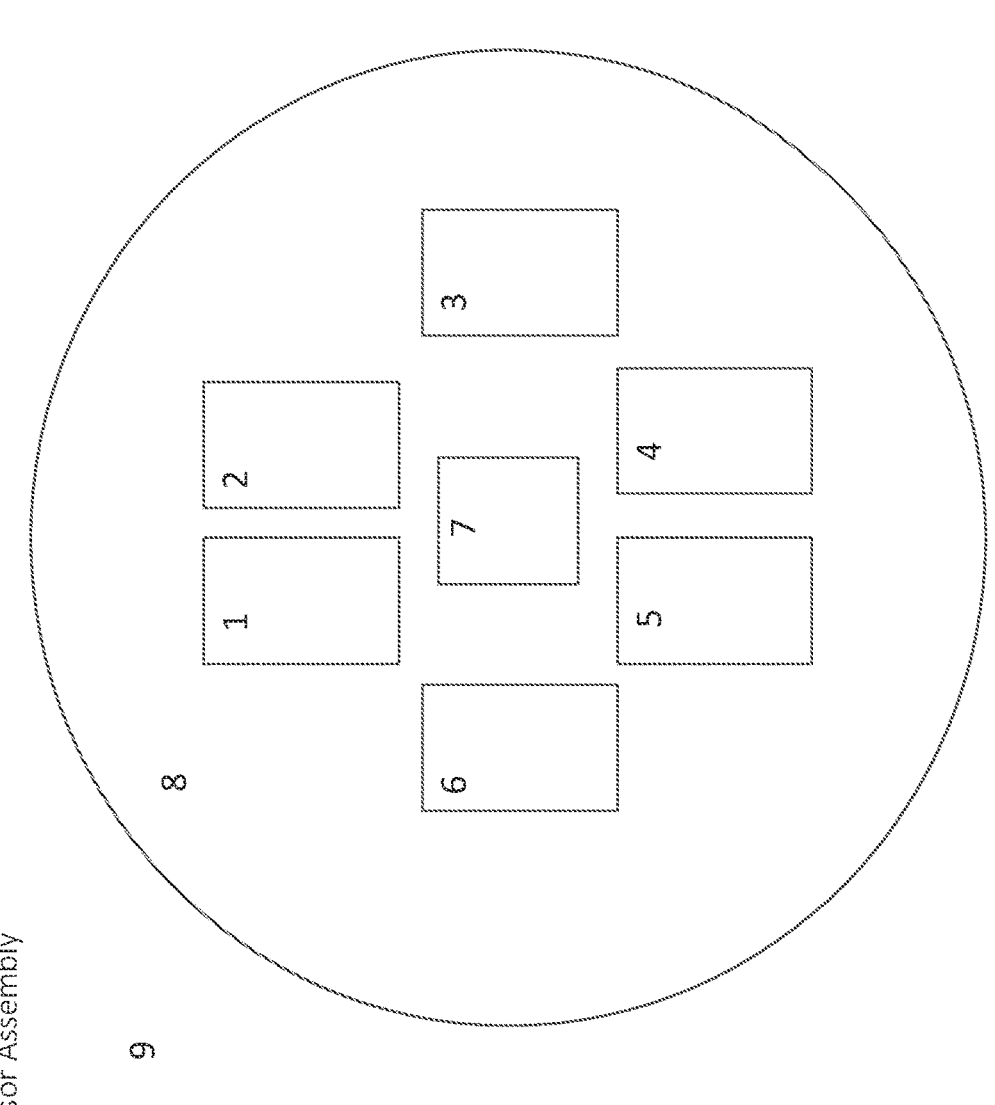
Sensor Assembly
9

9: sensor assembly
10: MCU
11: Bluetooth module
12: Accelerometer
13: ECG electronics module
14: First ECG Electrode
15: Second ECG Electrode
16: Ground ECG Electrode
17: SPO2 assembly
101: Power Supply
102: Battery Electronic Assembly

23

18: Green LED
19: Photodiode
20: Red LED
21: Infrared LED

22   SPO2 and PPG assembly

Wearable

27

23: Electronic Assembly
24: upper strap
25: lower strap
26: digital display

31: Filter 1050nm photodiode
32: Filter 1200nm photodiode
33: Filter 1300nm photodiode
34: Filter 1450nm photodiode
35: Filter 1550nm photodiode
36: Filter 1650nm photodiode
37: broad spectrum light 1050nm-1700nm
38: Mounting circuit board Sensor Assembly

HEALTH SENSOR USING MULTIPLE LIGHT EMITTING DIODES

CROSS-REFERENCE TO RELATED APPLICATIONS

The current application claims priority under 35 U.S.C. § 119(e) to provisional application Ser. No. 63/339,721 filed May 9, 2022, the disclosure of which is incorporated herein by reference in its entirety.

TECHNICAL FIELD

The present invention relates generally to health sensors, and more particularly to a wearable health sensor using multiple light emitting diodes for non-invasive sensing, monitoring and management of one or more health parameters or other biometrics.

BACKGROUND

Chronic health issues and disease are on the rise worldwide. Current estimates are that close to 9% of the world population is affected by diabetes, which is expected to rise to 10% by 2045. In addition to full diabetes, an estimated 352.1 million people worldwide are pre-diabetic, a figure which is expected to rise significantly in the coming years. Conditions like diabetes can be a contributor to many other diseases/conditions such as cardiovascular disease, nerve damage (neuropathy), problems with nausea, vomiting, diarrhea, constipation, erectile dysfunction, kidney damage (nephropathy), eye damage (retinopathy), potentially leading to blindness, cataracts, glaucoma, foot damage leading to toe, foot or leg amputation, skin conditions including bacterial and fungal infections, hearing impairment, Alzheimer's disease, and depression.

In the case of diabetes, high Blood Glucose (BG) levels (e.g., hyperglycemia) are toxic and cause serious health complications due to damage to the vessels that supply blood to vital organs. Hyperglycemia increases the risk of heart disease and stroke, kidney disease, vision problems, and nerve problems. Frequent self-monitoring of blood glucose levels is an important activity in treating diabetes allowing a person to modify their diet and exercise regimen to ensure that normal BG levels are maintained. Two conventional methods for monitoring include lancing the skin to obtain blood, or employing subcutaneous needle patches that can continuously read glucose levels. The lancet method is painful and expensive requiring a blood sample on an electrochemical test strip. The subcutaneous method is painless but expensive and inconvenient requiring a patch with a subcutaneous needle or other type of inserted component.

Blood glucose monitoring is only effective if it is done regularly. Regular blood glucose monitoring is an essential task in managing diabetes. Users are more likely to manage their condition if their blood glucose measurements are shared with health professionals, and accordingly, monitoring is key. For example, Type 2 diabetes can be treated with diet, exercise, rest, and healthy eating that avoids high glycemic foods.

Unfortunately, monitoring with conventional electrochemical-based test strips is expensive, today typically costing $1.00 for each test and requiring the user to lance their finger to obtain a drop of blood for the test. Newly emerging continuous glucose monitors employ a patch containing electronics and a small-short needle that penetrates the surface of the skin. These devices can frequently come off or separate from the user, and cannot be used bathing or swimming. Further, they are very expensive, typically costing $10/day or more.

Non-invasive analysis of various physical signals representative of health, like blood glucose levels, has been extensively studied, however what is needed is a wearable device and associated system for non-invasive analysis of health or physical variables such as blood glucose levels of the wearer.

SUMMARY

This document describes a system and method to test blood glucose using light, to overcome problems in other prior art solutions to non-invasive blood glucose monitoring and management. In some aspects, a device can employ near infrared diffuse reflectance spectrum analysis combined with a multi-layer artificial neural network to directly read health-related metrics, such as blood glucose levels, from the skin. This technique is non-invasive, inexpensive, and convenient. A wearable version of the device can continuously monitor BG levels without penetrating the skin.

A wearable system is described herein, which is configured for monitoring health of a wearer, and in particular the blood glucose levels of the wearer. The wearable system can also include technology to track various health parameters such as heart rate, heart rate variability, blood pressure, oxygen saturation, respiration rate, sleep levels, activity levels. The wearable system can include a device that can be worn on the wearer's wrist, carried on a wearer's person, worn on a chain or strap, or attached to some part of the wearer's body.

Information collected from the wearable system can be provided to the individual, stored on a server, and or shared with other health professionals. Along with such information, users can track other health journal information relating to food consumption, activities or other observances relating to a person's health. The information supplied by the wearable system, in combination with user-supplied information, can provide a more complete understanding of a person's health state, and which can be analyzed by the wearer or health professional to make health condition assessments and predictions.

A health wearable that tracks glucose, activity levels, sleep and related metrics can be used to store data in on a server. The server-based solution can be used to help provide health advice and can be used to share health information with a health professional.

In some aspects of the present disclosure, an apparatus for sensing health parameters data of a physical attribute of a person is described. The apparatus includes a sensor unit having a circuit board having a plurality of light emitting diodes (LEDs), each of the plurality of LEDs configured for providing light at a specific wavelength that is different from other LEDs of the plurality of LEDs. The sensor unit further includes logic connected with the circuit board and configured to activate the LEDs in a dynamic pattern, the dynamic pattern comprising an order, an interval, and an intensity of illuminating each LED based on conditions of the person sensed by the sensor unit. The sensor unit further includes one or more sensors, at least one of the sensors being configured to sense reflected light from at least one of the LEDs when activated, and including a filter configured to allow passage of the reflected light of each LED within their specific wavelength that is returned from the person to determine the health parameters data. The apparatus further includes an attachment mechanism configured to attach the sensor unit to a part of the person and place the sensor unit on a location of the part of the person.

In further aspects, the apparatus or a system as above can include a processor communicatively coupled to the circuit board and configured to predict the health metric representing the physical attribute of the user by using a machine learning algorithm and the sensed LED reflected data. In yet other aspects, each of the plurality of LEDs is configured for providing light at a specific wavelength within a range from 1000 nm to 1700 nm and which specific wavelength is different from other LEDs of the plurality of LEDs.

In still yet further aspects, a circuit board is not used to mount and position the LEDs or sensors to the part of the person and/or at the location of the part of the person. For instance, the LEDs and/or sensor can be integrated with, embedded with, or mounted onto a glass surface that abuts the location of the part of the person. Alternatively. The LEDs and/or sensor can be connected in a housing to simply abut the location of the part of the person.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

FIG. 1 illustrates a sensor assembly of a health parameters sensing system using near infrared light emitting diodes:

Like reference symbols in the various drawings indicate like elements.

DETAILED DESCRIPTION

Figure 2:
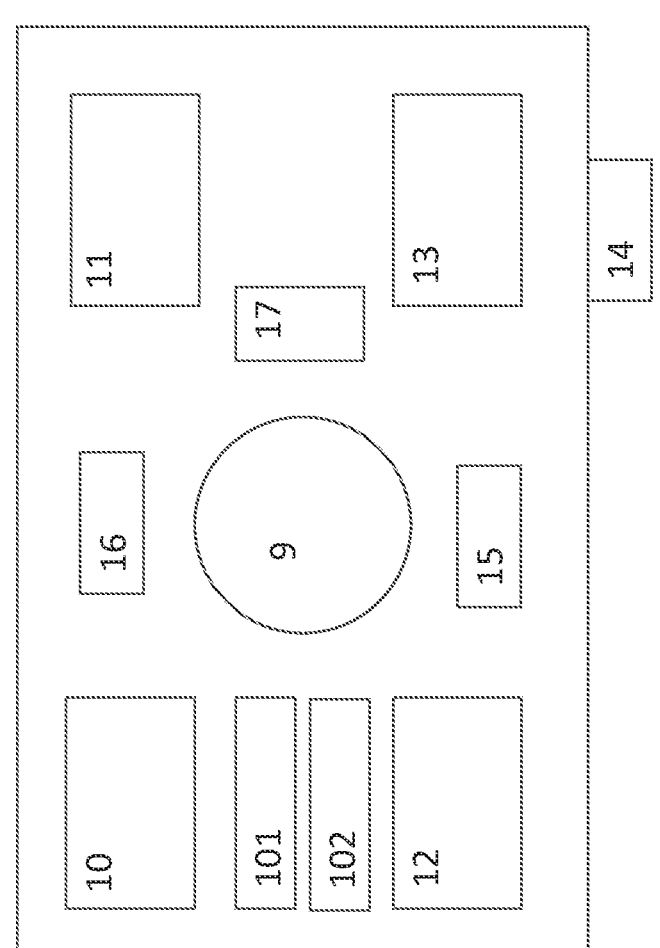
FIG. 2 illustrates an electronic assembly for powering and controlling the sensor assembly of the blood glucose estimation system.

This document describes systems and methods, employing a novel wearable device, to non-invasively sense, measure and monitor one or more health-related physical attributes of a wearer of the wearable device, in a pain-free manner. In some implementations, the wearable device can test for blood glucose (BG) levels using light from multiple light emitting diodes (LEDs) of different wavelengths that illuminates the wearer's skin in a dynamic pattern that includes an order, an interval, and intensity. The systems and methods described herein is painless, safe and inexpensive, and overcomes other prior art solutions to non-invasive blood glucose monitoring and management. The systems and methods utilize a device that is designed and configured to rest on the wearer's skin, and which uses a wireless communication technology to wirelessly transmit the wearer's sensed health data to a computing device such as a smartphone, tablet computer, laptop computer or desktop computer.

Other techniques that can be employed by a wearable device consistent with the present disclosure include, but are not limited to: polarimetry, photoacoustic spectroscopy, bio-electrical impedance spectroscopy, thermal emission, optics and other technologies. Optical techniques are recognized as highly accurate, painless and safe noninvasive glucose measurement techniques. Some methods can include optical coherence tomography, microwave spectroscopy, near-infrared spectroscopy (NIRS), midinfrared spectroscopy (MIRS), Raman spectroscopy and visible laser light. Near Infrared spectroscopy has the advantage of simplicity and effectiveness relative to other techniques. Near-infrared (NIR) components are cost-efficient and can penetrate the skin to adequate or suitable depths to enable accurate sensing and analysis.

In some implementations, a wearable device employs near infrared diffuse reflectance spectrum analysis combined with a multi-layer artificial neural network to directly read glucose levels from, or within, the wearer's skin. This technique is non-invasive, inexpensive, and convenient. A wearable version of the device can continuously monitor BG levels without penetrating the skin.

Electromagnetic waves have characteristic absorption levels for every element. This phenomenon is the basis for spectral analysis used in many industries. Exposing a sample to specific wavelengths and detecting the absorption levels allows one to determine the presence of specific elements. Combinations of elements produce absorption patterns that can be used to determine the presence of molecules based on their elemental composition. By comparing light intensity with absorption response, it is possible to determine levels of concentration. In practice, however, there are many factors that must be considered to use this technique as a viable measurement method within a consumer device.

In some implementations, a health monitoring system includes a wearable electronic apparatus. In some preferred implementations, the wearable electronic apparatus is configured to be worn on a body part, such as around an individual's wrist, in order to monitor and assess the individual's blood glucose level and can include other health data.

In some preferred exemplary implementations, a wearable device of a health monitoring system includes a band connected with an electronics module and configured to position the electronics module over the skin at a selected area of the body of a person. The wearable device further includes an output/display module in communication with a processor module for displaying any of the readings, ratings, and/or outputs to the person. The electronics module can further include at least one circuit board, a battery and a battery charging circuit.

In some implementations, the attachment structure is a band. The band can be configured to position the electronics module on a wrist of the user, or specifically, to position the electronics module in proximity with a blood vessel of the user. The attachment structure can further include a connector for receiving a smartwatch or other computing device. In some implementations, the connection is a pin connection.

The output module can be a display on the wearable device, and the display can be a multi-color, touch-sensitive, interactive organic LED (OLED) and/or liquid crystal display (LCD). The display can be configured to notify the user if the one or more sensors are ready to obtain readings, if the wearable device is converting the readings to output data, and if the wearable device has successfully completed collection of data from the sensors.

The output module can include a communication component for transmitting at least one of the calculated blood glucose and the collected data to a device external to the wearable electronic apparatus. In some implementations, the communication component is a wireless communication module, which can be a BLUETOOTH™ communication module or other near-field communication (NFC) module.

In some implementations, the wearable device can further include a collection of NIR LEDs arranged near or around one or more photodiodes, which photodiode is optimally tuned to, or sensitive to, wavelengths in the range 1050 nm to 1650 nm. The wearable device can further include a power supply, microprocessor and communications module allowing data to be sent to an external processing and/or display device. In some implementations, the wearable device sends light of specific wavelengths that are reflected by the skin, and which are then recovered by a single wideband photodiode. The microprocessor is connected with the one or more photodiodes to receive, process and interpret their sensed readings from the reflected NIR light provided by the NIR LEDs.

Power can be supplied to each LED of a sensor unit individually or one-at-a-time. The power can also be supplied according to a dynamic pattern, in which an order, an interval, and/or an intensity of illuminating each LED is based on conditions of the person sensed by the sensor unit. For instance, if the person is sweating, that is sensed and considered when powering an LED to achieve a target suitable intensity to compensate for the additional fluid between the person's blood and the sensor unit.

Once powered, the photodiode data is read from an amplifier circuit and an Analog to Digital (A/D) converter. This data can be fed into a deep learning artificial neural network (ANN) that has been trained to map the reading to a specific glucose measurement. In some implementations, the wearable device can be retrofit to existing wearable technologies. For example, the device can comprise a wristband peripheral, to be retrofitted to a watch, a smartwatch, or other complimentary wrist-worn wearable technology.

The output of the data readings and analysis can provide a health trajectory for the individual to predict a future state of health, as well as review the historical health trajectory from past sensed and measured states. In some implementations, the output of the data readings and analysis can be subject to an "auto-tagging" program where the device can determine the individual's behavior (such as eating, sleeping, exercising, or a state of stress) at a time point and attaching an electronic tag to that event. The auto-tagging program can also include a system, including hardware and software, whereby manual data can also augment and increase the individual's ability to capture additional details of personal relevance.

In preferred implementations, the data collected and amalgamated through the device can be subject to "machine learning" systems and methods to provide for predictive analysis for the individual, configured in a format to assist the individual in achieving personal health and wellness objectives. The data collected by the apparatus can apply psychometrics data analysis to assist the individual in achieving personal health and wellness objectives.

In preferred implementations, the output/display module is integral with the electronics module. In some alternatives, the output/display module is remote, but in communication with the electronics module. In other alternatives, the output/display module is a multi-color LED for providing individual interaction with device. The multi-color LED can be configured to let the individual know if health wearable data are ready to obtain the readings, if the apparatus is converting the readings to the outputs, and if the apparatus has successfully completed each measurement. The band can further include a connection to receive a smartwatch. In some implementations, the connection is a smartwatch pin connection.

Broadly stated, a method is provided for monitoring and assessing an individual's blood glucose levels. In preferred implementations, the method includes steps of providing a wearable electronic device as described herein (where the wearable electronic device includes one or more sensors or sensing devices and at least one processor); positioning the wearable electronic apparatus on the skin of an individual; taking, via the sensors, simultaneous measurements of heart rate, pulse wave velocity (PWV—a measure of arterial stiffness), and reflected light from LEDs within the blood glucose sensitive area; using the at least one processor to convert the heart rate, PWV measurements into a blood glucose estimate; and representing any of the readings, ratings, and/or outputs to the individual through the output/display module or transmitted to an external device.

In some implementations, the taking of the simultaneous measurements step is accomplished automatically using a timer. The output of the data readings and analysis can be subject to an auto-tagging and/or tagging program where the apparatus can determine the individual's behavior as an event (such as eating, sleeping, working out, or stress) and/or at a time point, and attach an electronic/digital tag to that event and/or time point. In some instances of the present disclosure, the output of the data readings and further analysis can provide a health trajectory for the individual to predict a future state of health.

According to another aspect, a wearable electronic apparatus for monitoring a user's blood glucose levels is disclosed. The apparatus comprises: an attachment structure for attaching the wearable apparatus to a predefined body location of the user; and an electronics module coupled to the attachment structure. In preferred implementations, the electronics module comprises: a plurality of sensors comprising at least a collection of LEDs and one or more photo diode; a processor module coupled to the plurality of sensors for collecting data therefrom and for calculating blood glucose using a machine learning method based at least one collected data; and an output module coupled to the processor module outputting at least one of the calculated blood glucose and the collected data.

The wearable apparatus can include a housing, formed in a low-profile so as to not be catchable to an object external to the person wearing the apparatus. The housing can be formed of a rigid or semi-rigid material, and can be formable to accommodate curves in the person at the location where the apparatus is attached or worn. In some implementations, the housing can include a combination of rigid and flexible materials to maximize flexibility yet protection of the components housed therein. In some implementations, a circuit board is not used to mount and position the LEDs or sensors to the part of the person and/or at the location of the part of the person. For instance, the LEDs and/or sensor can be integrated with, embedded with, or mounted onto a glass surface that abuts the location of the part of the person. Alternatively. The LEDs and/or sensor can be connected in a housing to simply abut the location of the part of the person.

FIG. 1 illustrates a sensor assembly of a health health parameter sensing system 9 using near infrared light emitting diodes, using six pulse LEDs, although more or less LEDs can be used depending on the health parameter data being sought. In the implementation illustrated, a first LED 1 is configured to emit a first light at a first wavelength, a second LED 2 is configured to emit a second light at a second wavelength, a third LED 3 is configured to emit a third light at a third wavelength, a fourth LED 4 is configured to emit a fourth light at a fourth wavelength, a fifth LED 5 is configured to emit a fifth light at a fifth wavelength, and a sixth LED 6 is configured to emit a sixth light at a sixth wavelength. A light sensor 7, such as a photodiode, is configured to receive at least a portion of the first light reflected from a skin of the user, a portion of the second light reflected from a skin of the user, a portion of the third light reflected from a skin of the user, a portion of the fourth light reflected from a skin of the user, a portion of the fifth light reflected from a skin of the user, and a portion of the sixth light reflected from a skin of the user. The LEDs 1-6 and light sensor 7 are arranged and mounted on a circuit board 8.

In some implementations, the first wavelength is about 1050 nm, the second wavelength is about 1200 nm, the third wavelength is about 1300 nm, the fourth wavelength is about 1450 nm, the fifth wavelength is about 1550 nm, and the first wavelength is about 1650 nm. In some embodiments any one LED may vary by +/−50 nm.

The electronics module can further include an accelerometer for collecting the movement data of the user. The processor module can calculate blood glucose using the machine learning method based on collected data and the user's historical health data.

FIG. 2 illustrates an electronic assembly 23 for powering and controlling a sensor assembly of a health parameters sensing system, such as shown in FIG. 1. The electronic assembly 23 includes the sensor assembly 9 as described above, and a microcontroller unit (MCU) 10 for controlling the sensor assembly 9. The assembly 23 can further include a BLUETOOTH™ module 11 or other wireless communication module, such as near field communications (NFC) or cellular communications, for communicating sensed data wirelessly to a device, such as a smartphone or mobile computer, external to the electronic assembly 23.

The electronic assembly 23 can also include further health parameters collection devices such as an accelerometer 12, electrocardiogram assembly (ECG electronics module 13, first ECG electrode 14, second ECG electrode 15, ground ECG electrode 16), and a pulse oximeter (SPO2) assembly 17. The electronic assembly also includes a power supply 101, such as a power plug connector or induction coil, and a battery 102, which is preferably rechargeable through the power supply 101. The battery 102 supplies electric power to the sensors, controller and processors of the system that is placed on a person.

Figure 3:
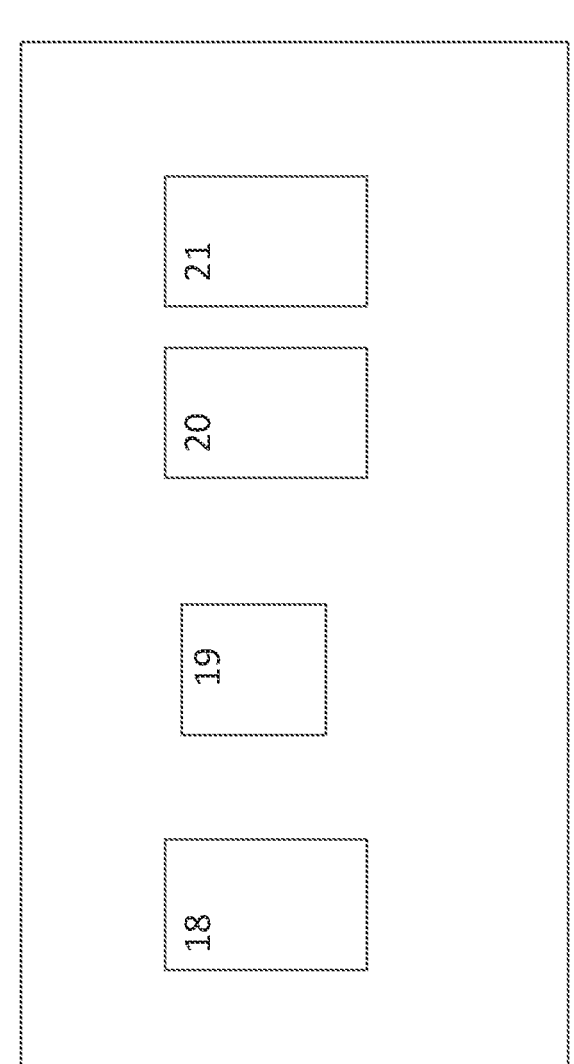
FIG. 3 illustrates an SPO2 and PPG assembly for a blood glucose estimation system using near infrared light emitting diodes amidst other light emitting diodes for other sensing applications.

The SPO2 assembly 17 and a PPG assembly 22 is shown in further detail in FIG. 3, having a green LED 18, a photodiode 19, a red LED 20 and an infrared LED 21.

Figure 4:
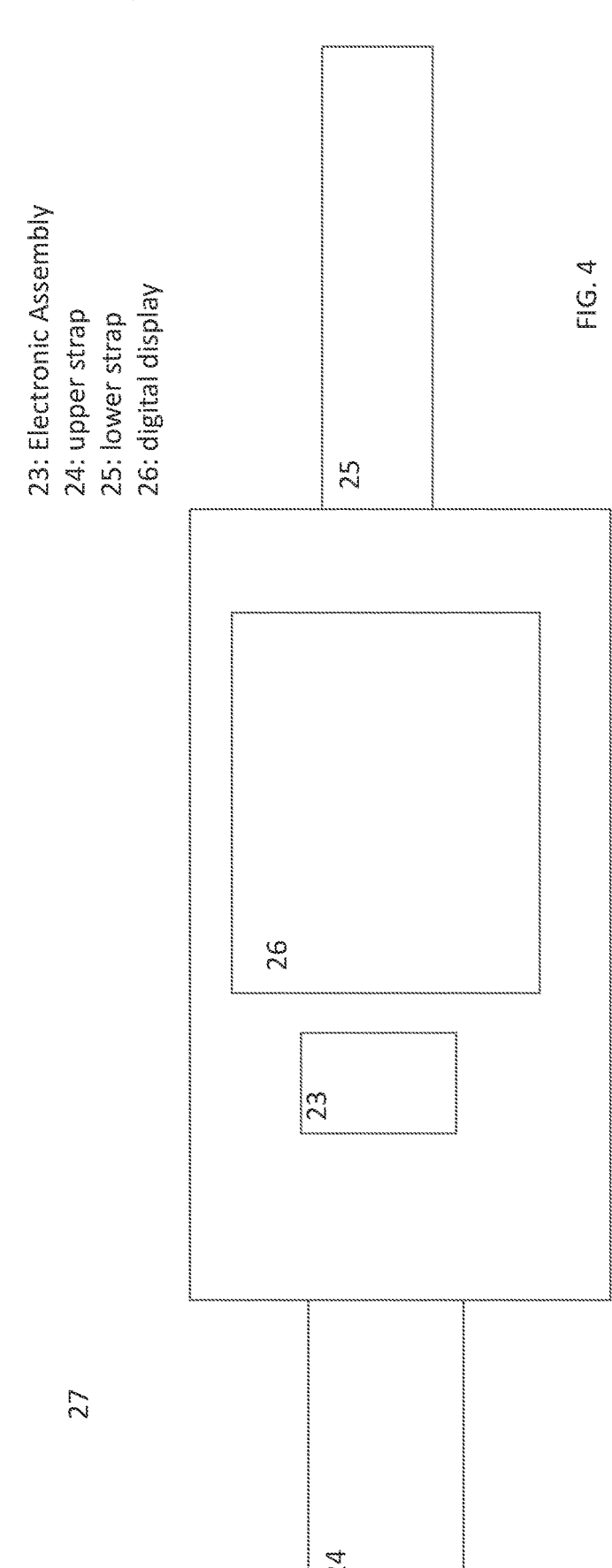
FIG. 4 illustrates a wearable device having a sensor assembly, electronic assembly, digital display and an attachment mechanism for attaching the wearable device to a person for sensing the person's health parameters, such as blood glucose levels, using multiple light emitting diodes.

FIG. 4 illustrates a wearable device 27 having a sensor assembly, electronic assembly 23, digital display 26 and an attachment mechanism 24, 25 for attaching the wearable device to a person for sensing the person's health parameters, such as blood glucose levels or other biometrics, using multiple light emitting diodes. The attachment mechanism 24, 25 can be a strap, such as a watch strap with upper strap 24 and lower strap 25. Alternatively, the attachment mechanism 24, 25 can be an adhesive or bubble-type attachment, configured to adhere to a specific area of the person at a particular contact pressure, while inhibiting lateral movement from the specific area of the person.

Figure 5:
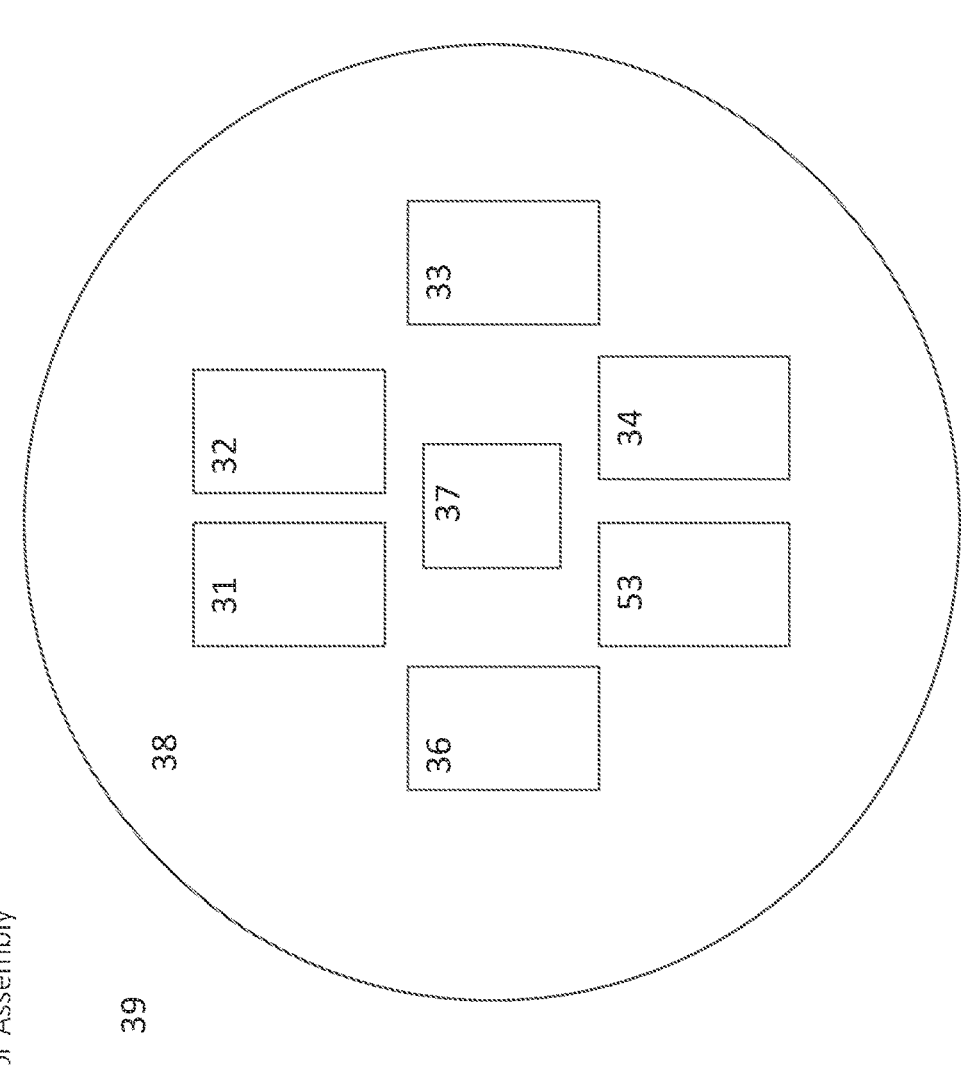
FIG. 5 illustrates a sensor and filter assembly of a health condition monitoring system.

FIG. 5 illustrates a sensor assembly of a health parameters sensing system 39, similar to the system shown in FIG. 1, but using near infrared filter photodiodes. In the implementation illustrated, a first filter photodiode 31 is configured to emit a first light at a first wavelength, a second filter photodiode 32 is configured to emit a second light at a second wavelength, a third filter photodiode 33 is configured to emit a third light at a third wavelength, a fourth filter photodiode 34 is configured to emit a fourth light at a fourth wavelength, a fifth filter photodiode 35 is configured to emit a fifth light at a fifth wavelength, and a sixth filter photodiode 36 is configured to emit a sixth light at a sixth wavelength. A broad spectrum light sensor 37 is configured to receive at least a portion of the first light reflected from a skin of the user, a portion of the second light reflected from a skin of the user, a portion of the third light reflected from a skin of the user, a portion of the fourth light reflected from a skin of the user, a portion of the fifth light reflected from a skin of the user, and a portion of the sixth light reflected from a skin of the user. The filter photodiodes 1-6 and light sensor 7 are arranged and mounted on a circuit board 8.

In some implementations, the first wavelength is about 1050 nm, the second wavelength is about 1200 nm, the third wavelength is about 1300 nm, the fourth wavelength is about 1450 nm, the fifth wavelength is about 1550 nm, and the first wavelength is about 1650 nm. In some embodiments, any one filter photodiode may vary by +/−50 nm.

Machine Learning

In preferred exemplary implementations of the present disclosure, a machine learning method is used. The machine learning method can be one or more of a polynomial regression analysis method, a neural network, a Bayesian network, a decision tree, an adaptive logic network, or a support vector machine.

According to another aspect of this disclosure, there is provided a method for monitoring a user's blood glucose levels. The method comprises: collecting data of the user using at least one sensor, the data comprising the blood glucose measurement apparatus; calculating blood glucose of the user using a machine learning method based at least one collected data; and outputting at least one of a calculated blood pressure data and the collected data.

In some implementations, a method of estimating or testing blood glucose levels includes steps of: emitting a first light at a first wavelength, a second light at a second wavelength, a third light at a third wavelength, a fourth light at a fourth wavelength, a fifth light at a fifth wavelength, a sixth light at a sixth wavelength; receiving at least a portion of the first light reflected from a skin of the user, and at least a portion of the second light reflected from a skin of the user, and at least a portion of the third light reflected from a skin of the user, and at least a portion of the fourth light reflected from a skin of the user, and at least a portion of the fifth light reflected from a skin of the user, and at least a portion of the sixth light reflected from a skin of the user; determining a first reading corresponding to the amount of the first light being absorbed by the blood under the skin and a second reading corresponding to the amount of the second light being absorbed by the skin, and a third reading corresponding to the amount of the third light being absorbed by the skin, and a fourth reading corresponding to the amount of the fourth light being absorbed by the skin, and a fifth reading corresponding to the amount of the fifth light being absorbed by the skin, and a sixth reading corresponding to the amount of the sixth light being absorbed by the skin; and calculating the blood glucose of the user using an artificial neural net.

In some alternative implementations, an apparatus and method employs and examines the absorption of light from a broad-spectrum light source that emits photons in the range from 1050 nm to 1650 nm. Accordingly, an arrangement of photodiodes can be used to read light through a person's skin. Similar to the blood glucose monitoring apparatus based on multi-source LEDs, absorption of light levels at specific frequencies is indicative of a blood glucose level based as determined by the Beer-Lambert law.

As shown in FIG. 5, an apparatus and system can include an arrangement of photodiodes around a central emitter. The emitter generates a light stream in a broad range of wavelengths from 1000 nm to 1700 nm. A series of photodiodes is positioned around the emitter. A filter is placed over each photodiode such that each photodiode can receive and detect a very narrow range of wavelengths. One variant of the apparatus uses filters for light at the following frequencies: 1050 nm, 1200 nm, 1300 nm, 1450 nm, 1550 nm and 1650 k. Other arrangements are possible.

In some implementations, each filter is physical device consisting of a small piece of plastic, glass or other semi-transparent material that has band gap filtering properties. The band gap filtering properties can be from the filter material itself, or from additional materials added to a base material. The filter material is engineered to only allow passage of light within a narrow bandwidth. In some implementations, an apparatus sends light with a wide band covering the full spectrum of NIR, and a collection of photodiodes are used with band gap filters to recover specific frequencies from the sample.

Although a few embodiments have been described in detail above, other modifications are possible. Other embodiments may be within the scope of the following claims.

The invention claimed is:

1. A continuous non-invasive sensor system having a multi-sensing detection device, the sensor system for employing characteristic spectral skin response data for determining a concentration of glucose being present in a tissue of a body of a wearer of the multi-sensing detection device, the system comprising:

a multi-sensing detection device being configured for being positioned proximate the skin of the wearer, the multi-sensing detection device having a glucose sensor unit for detecting glucose being present within the wearer's tissue, the multi-sensing detection device comprising:

a glucose sensor unit for detecting a characteristic spectral skin response of one or more tissues of the body due to a presence of glucose within the body tissue, the glucose sensor unit comprising:

a printed circuit board having a first and a second sensor assembly coupled therewith, each sensor assembly including a number of electromagnetic wave emitters and one or more electromagnetic wave receivers, each sensor assembly being arranged on the printed circuit board so as to be opposite the user's skin when the multi-sensing detection device is positioned on the user's body, each of the emitters being configured to dynamically emit, at a predetermined frequency, intensity, duration, and interval, the user's tissue with a determined range of electromagnetic waves, and each of the one more receivers configured to receive a return of the electromagnetic waves back from the user's tissue and to generate a return signal in response to collecting the returned electromagnetic waves, the first sensor assembly being configured for emitting microwaves for performing microwave spectroscopy and comprising a first set of electromagnetic wave emitters positioned so as to be proximate at least a first electromagnetic wave receivers, wherein the first electromagnetic wave receiver is configured for detecting the electromagnetic waves of the first set of electromagnetic wave emitters returned back from the body's tissues, and the second sensor assembly comprising a second set of electromagnetic wave emitters positioned linearly apart from one another on either side of at least a second electromagnetic wave receiver, wherein the second set of electromagnetic wave emitters are configured for emitting light waves and the second electromagnetic wave receiver is configured for detecting the electromagnetic waves emitted from the second set of electromagnetic wave emitters that is reflected back from the body's tissues, collectively the electromagnetic wave emitters of the first and second sensory assembly are configured for directing the emitted electromagnetic waves of their respective wavelengths into the tissue of the wearer, and the at least first and second electromagnetic wave receivers are configured for collecting the electromagnetic waves reflected back form the body tissue so as to generate the return signal, the printed circuit board further comprising an analog to digital converter coupled to the at least first and second electromagnetic wave receivers, the analog to digital converter being configured for converting the return signal to digital signal data, and a communications module for transmitting the digital signal data, a control unit coupled to the printed circuit board, the control unit configured to generate a pattern for dynamic emitter activation, whereby each emitter of the first and second sensor assemblies may be dynamically activated individually or collectively in one or more of a predetermined order, a predetermined time interval, a predetermined frequency, predetermined duration, and a predetermined intensity; and a server system for receiving the digital signal data from the multi-sensing detection device, the server system comprising:

a first processing module having a first processor for analyzing the dynamically generated digital signal data so as to produce spectral skin response data, and a second processor for analyzing the spectral skin response data so as to thereby determine the concentration of glucose being present in the tissue of the body of the wearer.

2. The continuous non-invasive sensor system in accordance with claim 1, wherein the pattern of dynamic emitter activation results in generating a corresponding pattern of absorption.

3. The continuous non-invasive sensor system in accordance with claim 2, wherein the pattern of absorption is based on a differential response of the skin to receipt of differential patterns of electromagnetic wave emittance.

4. The continuous non-invasive sensor system in accordance with claim 2, wherein the determination of the glucose concentration is based on the pattern of absorption.

5. The continuous non-invasive sensor system in accordance with claim 4, wherein the activation pattern is determined based on one or more health metrics of the wearer, and the server system includes a third processor configured for determining the health metrics of the wearer and for making a prediction regarding one or more physical attributes of the wearer based on the determined health metric.

6. The continuous non-invasive sensor system in accordance with claim 5, wherein the third processor implements an artificial intelligence executes a machine learning protocol.

7. The continuous non-invasive sensor system in accordance with claim 4, wherein the first set of emitters of the first sensor assembly are configured for emitting microwaves for performing the microwave spectroscopy.

8. The continuous non-invasive sensor system in accordance with claim 7, wherein the second set of emitters of the second sensor assembly comprises three photoemitters, further wherein the three photoemitters include a photoemitter formed of a light emitting diode configured for emitting green light, a photoemitter formed of a light emitting diode configured for emitting red light, and a photoemitter formed of a ninth light emitting diode configured for emitting near infrared light.

9. The continuous non-invasive sensor system in accordance with claim 7, wherein the second sensor assembly comprises a PPG sensor assembly for generating PPG results data.

10. The continuous non-invasive sensor system in accordance with claim 9, wherein the printed circuit board comprises an accelerometer for generating accelerometer results data.

11. The continuous non-invasive sensor system in accordance with claim 10, wherein the printed circuit board further comprises an SPO$_2$ assembly for generating SPO$_2$ results data.

12. The continuous non-invasive sensor system in accordance with claim 11, wherein the first processing module comprises an Artificial Intelligence module for implementing at least the first and second processors, and the determining of the concentration of glucose is further based on an analysis of the emitter data, PPG results data, accelerometer results data, and SPO$_2$ results data in addition to the analysis of the spectral data so as to thereby determine the concentration of glucose being present in the tissue of the body of the wearer.

13. The continuous non-invasive sensor system in accordance with claim 12, wherein the Artificial Intelligence module comprises a Machine Learning module and an Artificial Neural Network (ANN) for performing the recited analyses and for generating analyses results data.

14. The continuous non-invasive sensor system in accordance with claim 13, wherein the ANN maps the analyses results data to the concentration of glucose.

15. A continuous non-invasive sensor system having a multi-sensing detection device, the sensor system for employing a dynamically generated spectral skin response analysis for determining a concentration of an analyte being present in a skin tissue of a body of a wearer of the multi-sensing detection device, the system comprising:
    a multi-sensing detection device being configured for being positioned proximate the skin of the wearer, the multi-sensing detection device having an analyte sensor unit for detecting a specific analyte being present within the wearer's tissue, the multi-sensing detection device comprising:
    an analyte sensor unit for detecting a characteristic spectral skin response of one or more tissues of the body due to a presence of the analyte within the body tissue, the analyte sensor unit comprising:
        a printed circuit board having a first and a second sensor assembly coupled therewith, each sensor assembly including a number of emitters and one or more receivers, each sensor assembly being arranged on the printed circuit board so as to be proximate the user's skin when the multi-sensing detection device is positioned on the user's body, the one or more emitters configured to dynamically emit an electromagnetic wave, at a predetermined frequency, intensity, or interval of emission, into the user's tissue at a determined depth, and each of the one more receivers configured to receive a return of the emitted wave back from the user's tissue and to generate a return signal in response to collecting the returned electromagnetic wave,
        the first sensor assembly comprising a first set of emitters that are configured for emitting microwaves for performing microwave spectroscopy, wherein the first receiver is configured for detecting the electromagnetic waves of the first set of emitters returned back from the body's tissues, and
        the second sensor assembly comprising at least three or four photoemitters positioned so as to be proximate one or more photoreceivers, wherein the one or more photoreceivers is configured for detecting light of the three or four photoemitters of the second sensor assembly reflected back from the body's tissue, collectively the emitters of the first and second sensor assemblies being configured for directing the emitted electromagnetic waves into the skin of the wearer, and the at least first and second receivers are configured for collecting the electromagnetic waves returned back form the tissue so as to generate the return signal;
    an analog to digital converter being positioned on the printed circuit board and being coupled to the at least first and second receivers, the analog to digital converter being configured for converting the return signal into a digital signal data;
    a communications module coupled to the printed circuit board and being configured for accessing and transmitting the digital signal data; and
    a control unit coupled to the printed circuit board, the control unit being configured to generate a pattern for dynamic emitter activation, whereby each emitter of the first and second sensor assemblies may be activated individually or collectively in one or more of a predetermined order, a predetermined time interval, and at a predetermined intensity.

16. The continuous non-invasive sensor system in accordance with claim 15, further comprising a server system for receiving the digital signal data from the communications module of the multi-sensing detection device, the server system comprising a processing module having a first processor for analyzing the digital signal data so as to produce spectral data, a second processor for analyzing the spectral data so as to thereby determine a response of the skin to receipt of the electromagnetic waves generated by the pattern of dynamic emitter activation, and a third processor for determining the concentration of the analyte being present in the tissue of the body of the wearer based on the skin response.

17. The continuous non-invasive sensor system in accordance with claim 16, wherein the server system comprises an Artificial Intelligence module, and the Artificial Intelligence module is configured for receiving and analyzing data pertaining to the skin response so as to determine the concentration of the analyte present in the tissue of the body.

18. The continuous non-invasive sensor system in accordance with claim 17, wherein the second sensor assembly comprises a PPG sensor assembly having a number of LEDs comprising a green LED, a red LED, and an infrared LED emitter all configured for directing emitted light into the tissue of the body, as well as a photodiode that is configured for receiving reflected green, red, and infrared light back from the tissue so as to generate PPG results data.

19. The continuous non-invasive sensor system in accordance with claim 18, wherein the printed circuit board further comprises an accelerometer, for generating accelerometer results data, and a $SPO_2$ assembly, for generating $SPO_2$ results data.

20. The continuous non-invasive sensor system in accordance with claim 19, wherein the determining of the concentration of the analyte by the Artificial Intelligence module is further based on an analysis by the Artificial Intelligence module of one or more of the PPG results data, accelerometer results data, and $SPO_2$ results data in addition to the analysis of the skin response data so as to thereby determine the concentration of the analyte being present in the tissue of the body of the wearer.

\* \* \* \* \*